United States Patent
Levin et al.

(10) Patent No.: US 6,514,226 B1
(45) Date of Patent: Feb. 4, 2003

(54) METHOD AND APPARATUS FOR TREATMENT OF CONGESTIVE HEART FAILURE BY IMPROVING PERFUSION OF THE KIDNEY

(75) Inventors: Howard R. Levin, Teaneck, NJ (US); Mark Gelfand, New York, NY (US)

(73) Assignee: CHF Solutions, Inc., New York, NY (US)

(*) Notice: Subject to any disclaimer, the term of this patent is extended or adjusted under 35 U.S.C. 154(b) by 0 days.

(21) Appl. No.: 09/501,234

(22) Filed: Feb. 10, 2000

(51) Int. Cl.[7] ................................................. A61M 1/00
(52) U.S. Cl. .............................. 604/9; 600/16; 623/3.1
(58) Field of Search ............................... 604/4.01, 6.11, 604/8, 9, 131, 151, 507, 508; 128/898; 600/16; 623/3.1

(56) References Cited

U.S. PATENT DOCUMENTS

| | | | |
|---|---|---|---|
| 4,493,697 A | * 1/1985 | Krause et al. | ............... 604/522 |
| 4,535,757 A | 8/1985 | Webster, Jr. | |
| 4,710,164 A | 12/1987 | Levin et al. | |
| 4,762,820 A | 8/1988 | Garvas | |
| 4,927,407 A | * 5/1990 | Dorman | ....................... 600/16 |
| 5,045,057 A | 9/1991 | Van Driessche et al. | |
| 5,167,628 A | 12/1992 | Boyles | |
| 5,290,227 A | 3/1994 | Pasque | |
| 5,308,319 A | 5/1994 | Ide et al. | |
| 5,326,374 A | 7/1994 | Ilbawi et al. | |
| 5,332,403 A | 7/1994 | Kolff | |
| 5,385,548 A | 1/1995 | Williams et al. | |
| 5,395,330 A | 3/1995 | Marcadis et al. | |
| 5,444,083 A | * 8/1995 | Yamanaka et al. | ........... 514/429 |
| 5,505,701 A | 4/1996 | Anaya Fernandez de Lomana | |
| 5,536,237 A | 7/1996 | Prince et al. | |
| 5,620,418 A | 4/1997 | O'Neil | |
| 5,653,690 A | 8/1997 | Booth et al. | |
| 5,655,548 A | 8/1997 | Nelson et al. | |
| 5,695,457 A | 12/1997 | St. Goar et al. | |
| 5,720,726 A | 2/1998 | Marcadis et al. | |
| 5,755,779 A | 5/1998 | Horiguchi | |
| 5,776,190 A | 7/1998 | Jarvik | |
| 5,795,325 A | 8/1998 | Valley et al. | |
| 5,824,071 A | 10/1998 | Nelson et al. | |
| 5,869,539 A | 2/1999 | Garfield et al. | |
| 5,902,336 A | 5/1999 | Mishkin | |
| 5,911,702 A | 6/1999 | Romley et al. | |
| 5,957,880 A | 9/1999 | Igo et al. | |
| 6,086,527 A | 7/2000 | Talpade | ....................... 600/18 |
| 6,136,025 A | * 10/2000 | Barbut et al. | ................ 623/3.1 |
| 6,200,260 B1 | 3/2001 | Bolling et al. | |
| 6,390,969 B1 | 5/2002 | Bolling et al. | |

FOREIGN PATENT DOCUMENTS

DE     199 01 078     1/1999

OTHER PUBLICATIONS

Easton Associates, "Evaluation of the U.S. Market Opportunity for the SAFE System in Congestive Heart Failure", pp. 1–58 May, 2000.

(List continued on next page.)

Primary Examiner—J. Casimer Jacyna
(74) Attorney, Agent, or Firm—Nixon & Vanderhye P.C.

(57) ABSTRACT

A method for treating congestive heart failure (CHF) has been developed that restores kidney renal functions by artificially perfusion of at least one kidney. The kidney is perfused with the patient's blood or other suitable perfusion fluid. A catheter inserted into the aorta of the patient has a distal end that supplies the perfusion fluid into a renal artery of the patient. The catheter may be coupled to an implanted blood pump or to an external supply of perfusion pressure. The restoration of kidney function assists the heart by removing excess fluid, urine and toxin from the patient, and by normalizing the patient's renin-angiotensin system and other neurohormonal substances. The method is applicable to treat chronic and acute CHF.

19 Claims, 7 Drawing Sheets

OTHER PUBLICATIONS

Silverstein, Marc Elliot et al., "Treatment of Severe Fluid Overload By Ultrafiltration," New England Journal of Medicine, vol. 291, No. 15, Oct. 1974.

Simchon, S. et al., "A New Method for Kidney Perfusion in Situ: Application to Dynamics of Autoregulation", American Physiological Society, pp. 86–94, 1982.

Walker, Howard S.J., "Use of a Balloon–Tipped Perfusion Catheter for Renal Preservation During Suprarenal Abdominal Aortic Operations", pp. 337–339, 1985.

Trost, D et al., "Interventional Management of Ostial Lesions in the Renal Artery", pp. 88–102.

Tandan, Ved et al., "Renal Perfusion With the Biomedicus Pump During Resection of an Abdominal Aortic Aneurysm", pp. 634–636, Dec. 1992.

J. Lloveras et al., "Newly Developed Four–Lumen Catheter for In Situ Renal Perfusion of Non–Heart Beating Donors That Provides Perfusion Pressure Monitoring", Transplantation Proceedings, vol. 27, pp. 2909–2910, Oct. 1995.

Chandra, Nisha et al., "Vital Organ Perfusion During Assisted Circulation by Manipulation of Intrathoracic Pressure", Circulation, vol. 84, No. 1, pp. 279–286, Jul. 1991.

Ved Tandan et al, "Renal Perfusion With the Biomedicus Pump During Resection of an Abdominal Aortic Aneurysm", pp. 634–636.

Pawlik et al, Effects of Dimaprit, Prostacyclin, and Acetycholine on Renal Blood Flow and Function, *Proceedings of the Society for Experimental Biology and Medicine*, 163, 344–349 (1980), pp. 344–349.

* cited by examiner

METHOD AND APPARATUS FOR TREATMENT OF CONGESTIVE HEART FAILURE BY IMPROVING PERFUSION OF THE KIDNEY

FIELD OF THE INVENTION

The invention generally relates to the treatment of congestive heart failure (CHF). In particular, the invention relates to a method and apparatus to treat patients with congestive heart failure by normalization of kidney perfusion to restore to the patient the benefits of normal kidney functioning.

BACKGROUND OF THE INVENTION
A. Congestive Heart Failure (CHF)

Congestive heart failure (CHF) is a serious condition affecting an estimated 5 million Americans. Increasing prevalence, hospitalizations, and deaths have made CHF a major chronic health condition in the United States. There are an estimated 400,000 new cases of CHF each year. These cases are often first diagnosed as the end stage of cardiac disease. The average mortality rate of CHF is 10 percent after the 1st year and 50 percent after 5 years. Thus, half of the patients diagnosed with CHF will die within 5 years of their diagnosis.

The magnitude of the problem is expected to get much worse as more cardiac patients are able to survive and live longer. As patients live longer, the potential for developing CHF increases. In addition, because the incidence of heart failure rises substantially beyond age 65, the prevalence of this condition is likely to increase as the population ages.

The high prevalence of heart failure and the resulting high cost of caring for these patients places a significant economic burden on society. The American Heart Association statistics report that, including medications, an estimated $22.5 billion will be spent for the care of CHF patients in hospitals, physicians offices, home care, and nursing homes including medications in the year 2000. In light of the high costs and poor prognosis of CHF, there is a pressing need to prevent this condition and provide better clinical management to reduce morbidity and mortality.

Congestive heart failure (CHF) is a diseased condition in which the heart fails to function efficiently as a pump to provide sufficient blood flow and/or pressure to fulfill the normal circulatory needs of a patient. CHF is the primary reason for tens of thousands of deaths each year and is a contributing factor in an additional 200,000 more deaths. CHF results in sudden shortness of breath, fainting and irregular heart beats that require frequent emergency room treatments (acute CHF), and in its chronic form leads to repeated hospital stays, deteriorating quality of life and significant costs to the health care system. Congestive heart failure is characterized by: (1) signs and symptoms of intravascular and interstitial volume overload, including shortness of breath, fluid in the lungs, and edema, and (2) manifestations of inadequate tissue perfusion, such as fatigue or poor exercise tolerance. These signs and symptoms result when the heart is unable to generate a cardiac output sufficient to meet the body's demands.

A healthy heart pumps blood by increasing the kinetic energy (pressure and/or velocity) of the blood flowing through a person's circulatory system. The energy imparted by a heart to the blood flow is normally sufficient to cause the blood to circulate through the lungs, kidney and other organs of the body. A failing heart is generally unable to maintain normal blood pressure within the circulatory system of a person. The body responds to a failing heart by diverting much of the available blood flow to the brain and heart and reducing the blood flow to other body organs, including the kidneys. Thus, the body acts to save the brain (which cannot survive more than a few minutes of inadequate blood flow).

The heart ejects oxygen-enriched blood into the aorta, which is a huge blood vessel, from which branches all other arteries that lead to the different organs of the body. These organs use the oxygen from the arterial blood. Used blood deprived of oxygen and containing the metabolic byproduct carbon dioxide is collected from the organs via individual veins and is returned to the lungs via the pulmonary vein. Accordingly, the heart pumps the blood into the aorta and forces the blood to circulate through the arteries, organs, veins and lungs.

Arteries by expanding or contracting regulate the blood supply flowing to individual tissues and organs. Arterial walls are made of thin layers of muscle fibers that expand and contract. The expansion and contraction of the arteries controls the flow of blood through a patient's circulatory system in a manner similar to the way valves control the flow of water through the water pipes in a home. The arterial walls contract or relax responding to different stimuli decreasing or increasing the inner cross section of the vessel. The contraction of the arteries is called vasoconstriction and the relaxation is called vasodilation. In this manner, depending on the oxygen needs of an organ or tissue, arterial blood flow is controlled and the supply of oxygen rich blood is regulated. Only as much arterial blood as needed is supplied to organs depending on the functions they are performing at the time.

When the demand for oxygen delivery from the blood exceeds the available blood supply for a particular organ, the organ becomes ischemic (which is a condition in which minimized blood flow can lead to oxygen starvation of an organ). If allowed to persist, ischemia leads to severe tissue damage. The complex network of neurohormonal messengers indicates to the brain that the blood supplied by the heart and the blood vessels is not sufficient to support the current metabolic needs of that organ. The body reacts to ischemic by supplying more blood to the organ(s) needing more oxygen in order of priority. For example, the legs of a human runner get more blood during exercise because the leg muscles are working hard and need extra oxygen. Similarly, the runner's gut receives an increase of blood flow when food is digested. If the runner tries to eat and run at the same time, he may get cramps in the legs or stomach pain because of ischemia. The brain reacts by altering the autonomic nervous system activity and neurohormonal secretions to attempt to divert additional blood flow from other organs to augment the blood supply to the ischemic organs to meet their metabolic demands. Accordingly, in a healthy patient, the circulatory system is adjusted by the brain so that all organs receive adequate blood supply. However, the body cannot supply adequate blood flow to all organs when the heart begins to fail during CHF. The ultimate priority for the body is always to maintain sufficient blood pressure in the aorta at any cost to protect the brain.

Heart failure is not simply a disease of the heart, but rather is a complex disease process that involves interaction of many of the body's systems. It is believed that the body reaction to a signal of low blood pressure is based on the body's interpretation that it has suffered a severe injury that caused massive bleeding. In this situation, the body attempts to reduce the probability of death from low blood pressure by diverting blood flow away from the organs that can temporarily tolerate ischemia (e.g., the body extremities, liver and kidneys) to the vital organs (brain and heart) that cannot tolerate even momentary ischemia (such as the brain and heart). In the situation of bleeding, if the bleeding stops in a brief amount of time, the blood pressure will rise in the circulatory system. As blood pressure rises, the body will restore normal blood flow through the entire circulatory system and to all body organs. It appears that evolution has adapted the human body to react to severely reduced blood pressure by temporarily reducing blood flow to less vital organs such as limbs, gut or kidney. This reaction assumes that normal blood pressure will be quickly restored or the person will die from their injuries.

This same originally beneficial evolutionary reaction to reduced blood pressure appears to be deleterious in the setting of congestive heart failure. Congestive heart failure is not relieved by reducing blood flow to body organs and body exterminates. In fact, CHF is not a temporary reduction in blood pressure, but instead is characterized by reduced blood pressure for weeks, months and years of a patient's life. Moreover, CHF is a relatively recent condition to which the body has not adapted by evolution. Accordingly, it is believed that the body's response in CHF causes many body organs, such as the kidney, to receive inadequate blood flow for too long a period of time. As these organs shut down due to inadequate blood flow, they are no longer able to perform their normal physiological functions.

Congestive heart failure can be either acute and/or chronic. Acute CHF occurs suddenly and often requires emergency treatment. Chronic CHF is a slowly deteriorating condition that continuously worsens and often requires repeated treatments in the hospital.

In both conditions the failing heart is not be able to generate sufficient blood pressure to properly perfuse the kidneys, e.g., provide sufficient blood pressure to force blood through the kidneys and filter the blood. In a patient suffering form chronic heart failure, the blood pressure tends to progressively decrease as the heart progressively fails over weeks, months and/or years. With the decrease in blood pressure there is a concomitant decrease in organ perfusion. Accordingly, chronic heart failure can lead to chronic impaired renal perfusion. Treatments for chronic CHF must be able administered repeatedly to a patient, preferably in a clinic or other no intensive critical-care unit (ICU) of a hospital without causing injury to the patient or reduce the physician's capacity to perform repeated therapy.

Chronic heart failure patients are frequently admitted to hospital with an abrupt worsening of their condition that requires intensive care (termed, acute heart failure). During these periods of acute hypotension (or low blood pressure) their kidneys are particularly at risk from hypotension and can be severely injured. In some cases the blood pressure of these patients can be normal but at the expense of the total shutdown of the blood flow to the kidneys. Kidneys of these patient are as much (or more) in jeopardy as the ones of the patients with low blood pressure. Because of its emergency nature, treatments of acute CHF must be fast-acting and thus may be extremely invasive and may require the patient to be admitted to an ICU. Thus, the apparatus for treating acute CHF are often fast acting and quickly administered, which may result, for example, in a rapid surgical insertion of a large catheter into an artery of the patient. The apparatus suitable for treating acute CHF may not be appropriate for repeated courses of treatments required for patients with chronic CHF. Because repeated treatments are required, the apparatus for treating chronic CHF should be adapted to be applied to the patient without the need for surgery or invasively entering the circulatory system under fluoroscopy that requires catheterization lab equipment. Accordingly, a different apparatus may be needed for treating chronic and acute CHF, even though the same method of treatment, e.g., perfusing a kidney, is performed by both apparatus.

B. Relationship Of Kidney Failure To CHF

The kidneys are a pair of organs that lie in the back of the abdomen on each side of the vertebral column. They play an important regulatory role in maintaining the homeostatic balance of the body. The kidneys function like a complex chemical plant. The kidneys eliminate foreign chemicals from the body, regulate inorganic substances and the extra-cellular fluid, and function as endocrine glands, secreting hormonal substances like renin and erythropoietin.

The main functions of the kidney are to maintain the water balance of the body and control metabolic homeostasis. The kidneys regulate the amount of fluid in the body by making the urine more or less concentrated, thus either reabsorbing or excreting more fluid, respectively. A large amount of blood (approximately 1,500 liters per day) passes through the kidneys. Of that, about 98% of the filtered fluid is reabsorbed. In addition, the kidneys extract undesirable chemicals and concentrate them in urine, while allowing the reabsorbtion of other chemicals. These processes of filtration, reabsorbtion and fluid regulation take place in the renal nephron. Within the nephron the smallest circulatory vessels, capillaries and arterioles, form a glomerulus. This glomerulous is intimatelly associated with the renal tubules to filter wastes from the blood, remove excess water from the body and produce concentrated urine. The glomerular filtration rate (GFR) is a clinical indicator universally accepted as a measure of the ability of the kidney to remove fluid and solutes. In other words, GFR is the summary of the physiologic functions of the kidneys.

A kidney, like any other organ, needs oxygen from the blood stream to function. The kidneys remove only a small amount of amount of the deleterious metabolic products from each portion of the blood to which they exposed. Thus, the blood is repeatedly circulated through the kidney many times during each day to remove the required amount of these substances. Under normal conditions in a healthy person, the kidney must receive approximately 10% of the cardiac output (total body blood flow) or 0.5 liters per minute which, over the course of a day, amounts to 720 liters per day of blood passing through each kidney. Significantly, more fluid is filtered through the kidneys than is excreted as urine. Most of the filtered fluid must be reabsorbed into the circulatory system to maintain the fluid balance of the body. In case of CHF, some normal and important physi-ological functions become detrimental to the patient's health. This process is sometimes called maladaption.

Without properly functioning kidneys, a patient will suffer water retention, reduced urine flow and an accumulation of wastes toxins in the blood and body. These conditions resulting from reduced renal function or renal failure (kidney failure) are believed to increase the workload of the heart. In a CHF patient, renal failure will cause the heart to further deteriorate as the water build-up and blood toxins accumulate due to the poorly functioning kidneys and in turn, cause the heart further harm.

Figure 6:
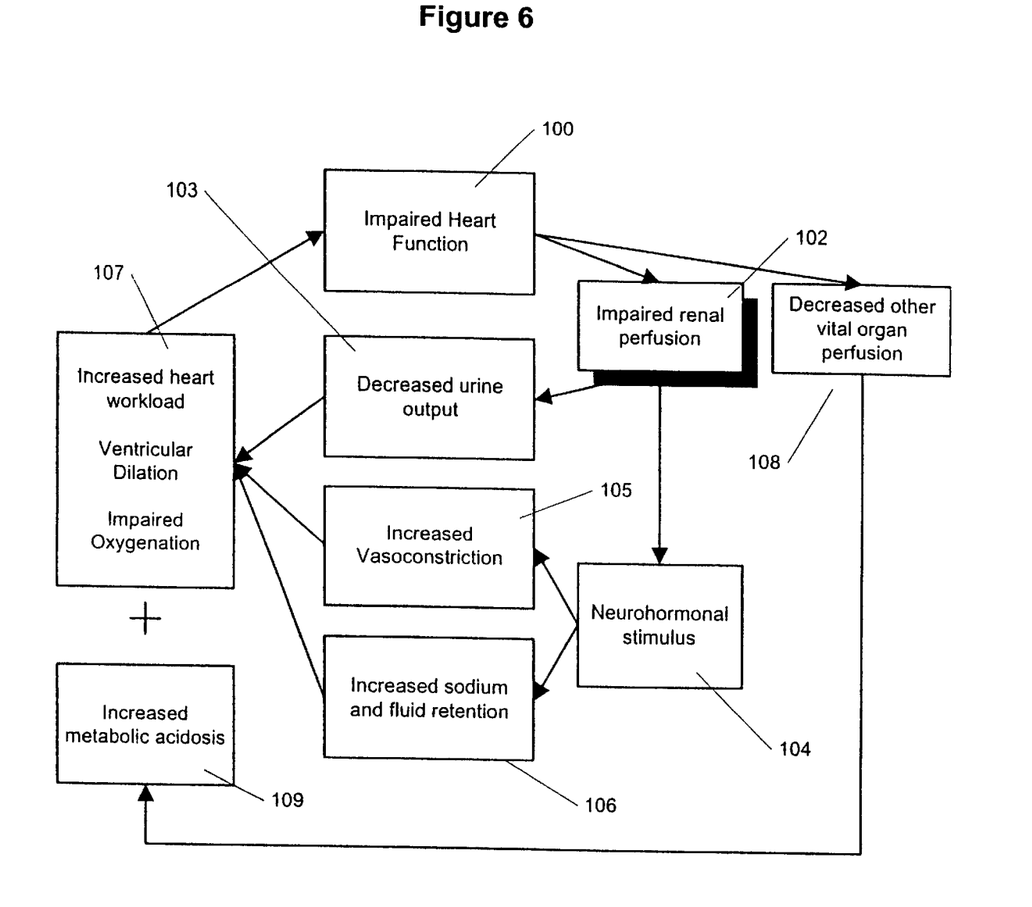
FIG. 6 is a flow diagram of the compensatory cycle of congestive heart failure.

FIG. 6 is a chart that illustrates the cycle of CHF as it relates to renal failure of the kidneys. In step 100 of CHF, for any of the known cause of heart dysfunction, the heart will progressively fail and blood flow and pressure will drop in the patient's circulatory system. In the acute heart failure, the short-term compensations serve to maintain perfusion to critical organs, notably the brain and the heart that cannot survive prolonged reduction in blood flow. In chronic heart failure, these same responses that initially aided survival in acute heart failure can become deleterious.

A combination of complex mechanisms contribute to the deleterious fluid overload in CHF. As the heart fails and blood pressure drops, the kidneys cannot function owing to insufficient blood pressure for perfusion and become impaired in step 102. This impairment in renal function ultimately leads to a decrease in urine output in step 103. Without sufficient urine output, the body retains fluids and the resulting fluid overload causes peripheral edema (swelling of the legs), shortness of breath (from fluid in the lungs), and fluid in the abdomen, among others undesirable conditions in the patient.

In addition, the fall in cardiac output leads to reduced renal blood low, increased neurohormonal stimulus, and release of the hormone renin from the juxtaglomerular apparatus of the kidney, in step 104. This results in avid retention of sodium and thus volume expansion, 106. Increased rennin results in the formation of angiotensin, a potent vasoconstrictor, 105.

Heart failure and it's the resulting reduction in blood pressure reduces the blood flow and perfusion pressure through organs in the body 108, other than the kidneys. As these other organs suffer reduced blood pressure, these organs may become hypoxic causing the development of a metabolic acidosis 109 which reduces the effectiveness of pharmacological therapy as well as increases the risk of sudden death This spiral of deterioration that physicians observe in heart failure patients is believed to be mediated in large part, by activation of a subtle interaction between heart function and kidney function, known as the renin-angiotensin system. Disturbances in the heart's pumping function results in decreased cardiac output and diminished blood flow 100. The kidneys respond to the diminished blood flow as though the total blood volume was decreased, when in fact the measured volume is normal or even increased 102. This leads to fluid retention by the kidneys 106 and formation of edema causing fluid overload and increased stress on the heart 107.

Systemically, CHF is associated with an abnormally elevated peripheral vascular resistance and is dominated by alterations of the circulation resulting from an intense disturbance of sympathetic nervous system function. Increased activity of the sympathetic nervous system promotes a downward vicious cycle of increased arterial vasoconstriction (increased resistance of vessels to blood flow) followed by a further reduction of cardiac output, causing even more diminished blood flow to the vital organs.

In CHF via the previously explained mechanism of vasoconstriction, the heart and circulatory system dramatically reduce blood flow to kidneys. In addition, during CHF the kidneys receive a command from higher neural centers via neural pathways and hormonal messengers to retain fluid and sodium in the body. In response to stress on the heart, the neural centers command the kidneys to reduce their filtering functions. While in the short term these commands can be beneficial, if these commands continue over hours and days they can jeopardize the persons life or make the person dependent on artificial kidney for life by causing the kidneys to cease functioning.

When the kidneys do not fully filter the blood, a huge amount of fluid is retained in the body resulting in bloating (fluid in tissues), and increases the workload of the heart. Fluid can penetrate into the lungs and the patient becomes short of breath. This odd and self-destructive phenomenon is most likely explained by the effects of normal compensatory mechanisms of the body that improperly perceive the chronically low blood pressure of CHF as a sign of temporary disturbance such as bleeding.

In an acute situation, the organism tries to protect its most vital organs, the brain and the heart, from the hazards of oxygen deprivation. Commands are issued via neural and hormonal pathways/messengers. These commands are directed toward the goal of maintaining blood pressure to the brain and heart, which are treated by the body as the most vital organs. The brain and heart cannot sustain low perfusion for any substantial period of time. A stroke or a cardiac arrest will result if the blood pressure to these organs is reduced to unacceptable levels. Other organs, such as kidneys, can withstand somewhat longer periods of ischemia without suffering long-term damage. Accordingly, the body sacrifices blood supply to these other organs in favor of the brain and the heart.

The hemodynamic impairment resulting from CHF activates several neurohomonal systems, such as the rennin-angiotensin and aldosterone system, sympatho-adrenal system and vasopressin release. As the kidneys suffer from increased renal vasoconstriction, the filtering rate (GFR) of the blood drops and the sodium load in the circulatory system increases. Simultaneously, more renin is liberated from the juxtaglomerular of the kidney 104. The combined effects of reduced kidney functioning include reduced glomerular sodium load, an aldosterone-mediated increase in tubular reabsorption of sodium, and retention in the body of sodium and water. These effects lead to several signs and symptoms of the CHF condition, including an enlarged heart, increased systolic wall stress and an increased myocardial oxygen demand, and the formation of edema on the basis of fluid and sodium retention in the kidney 107. Accordingly, sustained reduction in renal blood flow and vasoconstriction is directly responsible for causing the fluid retention associated with CHF.

Fluid overload is caused in two ways. First, activation of the renin-angiotensin system leads to retention of salt, thus water by the kidney. Second, the persistent lower renal blood flow and pressure cannot generate adequate hydrostatic pressure to make sufficient urine to remove excess retained fluid. Accordingly, the kidneys are a principal non-cardiac cause of a progressive fluid overload condition in a patient suffering from CHF.

C. Prior Treatments for CHF

Many non-surgical therapies are widely used to treat CHF. In general, they include methods of increasing the pumping ability of the heart itself or reducing the work required of the heart to pump blood. These therapies are effective at first but their effects are ultimately exhausted. In addition, no non-surgical therapies have been able to prevent the inexorable decline in circulatory function.

The principal disturbance in CHF is the inability of the heart to perform as a pump leading to a reduced cardiac output. Thus, directly combating the inability of the heart to propel blood forward might seem to be the single most intuitive means for treating heart failure. Utilizing this mechanism, a class of drugs known as inotropes increases the strength of contraction of the heart, allowing the heart to expel more blood with each beat. However, while effective in the short-term, these drugs lack long-term value in the treatment of congestive heart failure.

Patients with CHF can also suffer episodes of acute, severe deterioration caused by abrupt decreases in heart function. These episodes are characterized by rapid reductions in blood pressure and flow, especially to the kidney.

Similarly to the chronic state, acutely reduced kidney perfusion can result in a sudden, massive retention of fluid leading to pulmonary edema (fluid in lungs). This acute fluid overload taxes an already overburdened heart and can lead to the severest of complications: acute renal failure and death.

In the intensive care unit, these patients may benefit from short-term use of inotropic therapy (drugs that improve the ability of the heart to squeeze and pump blood) to temporarily improve cardiac output and renal blood flow. Intubation and mechanical ventilation of the lungs are of value in patients with severe hypoxia from fluid overload leading to pulmonary edema. Mechanical ventilation is very effective but is complicated by infections and difficulty in weaning patients off the ventilator. Patients with severe refractory pulmonary edema may also benefit from intra-aortic balloon counterpulsation to assist the heart. However, while very effective in treating refractory angina, intra-aortic balloon pumping has not been shown to have a significant beneficial clinical effect in acute CHF. The inotropic drugs may cause severe arrhythmias (irregular heart beats) that can also lead to death.

Increasing doses of more powerful intravenous diuretics may be used but are increasingly ineffective as the renal perfusion is reduced in response to the maladaptive compensatory response. Over time as heart function further decreases and vasoconstriction further increases, progressively less blood reaches the kidneys, resulting in a progressive inability to excrete fluid and increasingly severe symptoms of fluid overload. Any degree of intrinsic renal insufficiency will also contribute to limiting the effectiveness of diuretic therapy and the patient will continue to retain fluid.

To treat CHF, the physicians must fight the body's attempt to inflict itself harm. Heart failure patients are put on a strict low sodium diet and their fluid intake is monitored. Some patients are limited to as little as one liter of fluid a day. The most important drugs in the physician's arsenal to combat fluid overload are the class of drugs called diuretics. Diuretics affect the kidney function in such a way that the reabsorbtion of fluid is suppressed. As a result there is more urine output contrary to neurohormonal commands that the kidney is receiving.

Physicians can treat the patient with agents that improve the pumping ability of the heart, increase blood pressure and attempt to reactivate a more normal behavior of the body's control (homeostatic) system. In general, this is effective in sustaining life of many heart failure patients. Nevertheless, in hundreds of thousands of patients, treatments with drugs and diet alone fail. The patients are repeatedly admitted to the hospital for intensive care. Ultimately they may require a heart transplant.

When available treatment can no longer achieve adequate fluid removal with existing kidney function, renal replacement therapies such as hemofiltration or dialysis have been increasingly used as a method of removing fluid in the acute CHF state. Acute heart failure can be treated with the Continuous Renal Replacement Therapy (a.k.a, an artificial kidney or dialysis machine) in the ICU of a hospital. The machine is instrumental in reducing fluid overload and preventing such complications as pulmonary edema. At the same time the kidney machine can be harmful to other organs and does not protect the kidney itself from further deterioration from the persistently low blood pressure and poor perfusion caused by vasoconstriction of the renal artery and arterioles (smaller branches). Thus, renal replacement therapy may be used to remove fluid but is associated with significant complications. Its use is limited since it may cause further abrupt reductions in blood pressure, actually worsening the heart failure state and further renal dysfunction. Physicians are reluctant to use it in unstable patients because of added risk of hypotension.

Continuous hemofiltration is a new modality based on a well-established therapy with an artificial kidney (or renal replacement therapy). Blood is continuously extracted from the body, passed through an artificial kidney machine and then returned back to the body. In the process, some of the undesired chemicals can be extracted. Most importantly for acute heart failure patients, fluid can be filtered out of the blood stream in a slow controlled infusion while concentrating the blood.

Blood is a suspension of cells in a fluid called plasma. Plasma contains water and chemicals. The artificial kidney machine allows a physician to control the separation of plasma and adjust the total amount of fluid remaining in the patient's body. The hemofiltration machine works in parallel with patient's kidneys and takes over their function.

The artificial kidney does nothing to protect natural kidneys from deterioration and as a result the natural kidneys often suffer progressive damage from hypotension and ischemia. Also, the artificial kidney does not interrupt the renin-angiotensin feedback mechanisms that continue to fight the physician in his or her attempts to save the patient from continued deterioration.

Reversing fluid overload can improve heart function and significantly enhance the clinical status of the CHF patient. Yet, while therapies that improve renal blood flow are beneficial in removing fluid, they are still relatively ineffective. Similarly, while therapies, such as hemofiltration, effectively remove fluid from the patient, they can actually lead to lower blood pressure, further deterioration of the heart and ultimately renal failure requiring the patient to undergo permanent dialysis or kidney transplant.

There is a long-felt need to be able to treat the fluid overload complications of CHF by being able to restore kidney function, without resorting to kidney dialysis. Restoration of kidney function should: (1) return kidney function to normal therefore protecting kidney from hypotension induced damage, (2) remove excess fluid volume from a patient in a safe controlled manner, and/or (3) alter a patient's neurohormonal environment. Such CHF treatment should decrease or eliminate the physical signs and symptoms of congestive heart failure, improving both a patient's quality of life and survival rate. The present invention provides a method to reduce the morbidity and mortality associated with congestive heart failure in patients by restoration of renal perfusion pressure.

SUMMARY OF THE INVENTION

Figure 7:
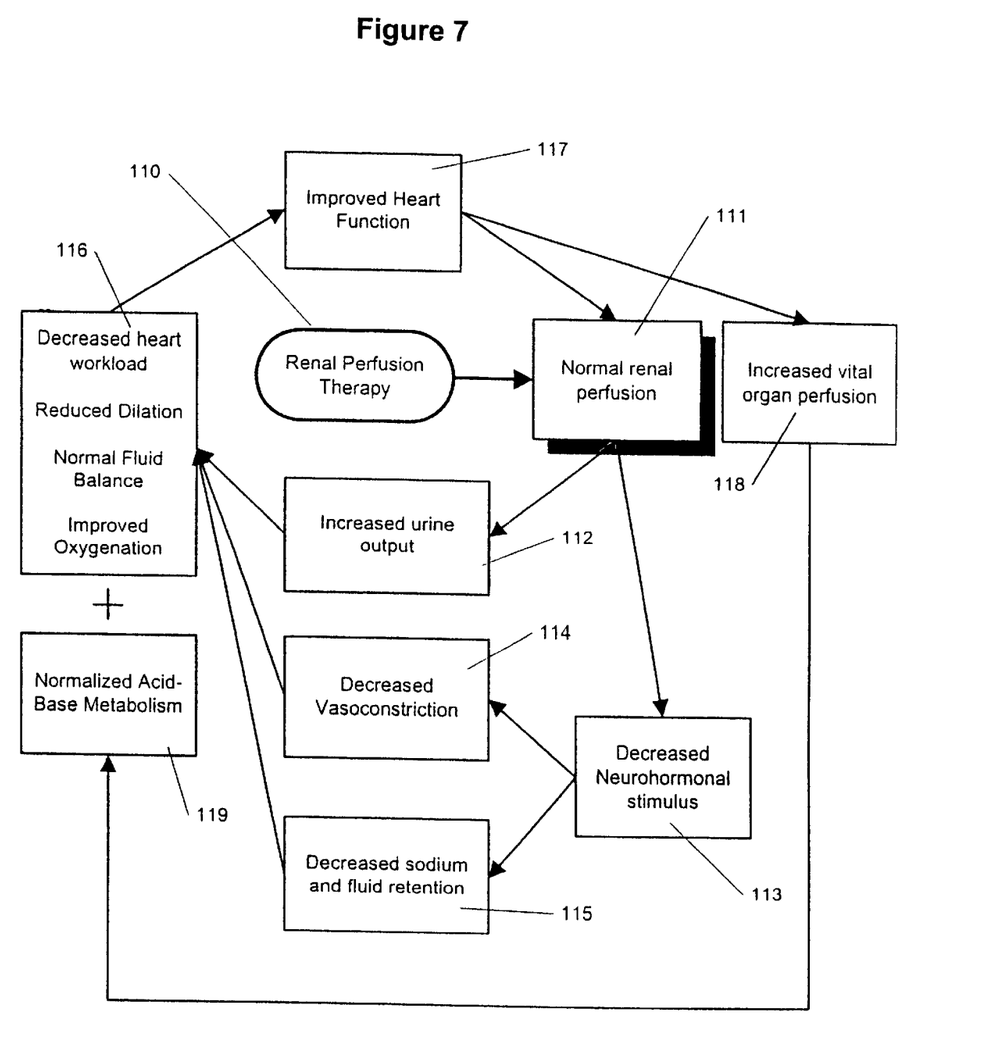
FIG. 7 is a flow diagram and illustration of the remedial effects of direct renal perfusion therapy on the cycle of CHF.

The invention is a novel method and apparatus of treating acute and chronic CHF by restoration of renal perfusion pressure. Restoration of acceptable blood pressure applied directly applied to one or both kidneys of a patient with heart failure significantly improves renal blood flow, removes excess body fluids and improve the patient's overall condition. In addition, restoring renal perfusion pressure to the kidney suppresses, the deleterious activation of the renin-angiotensin system and the consequences of its widespread adverse effects on CHF patients as is shown in FIG. 7. Increased fluid removal results from the restoration of a hydrostatic gradient 110 across the kidney by increasing renal blood flow under increased renal perfusion pressure. The level of effectiveness of this method is substantially above the levels achieved by drug therapy.

Restoring renal perfusion 111, should result in increased urine output 112 and a decrease in the neurohormaonal stimulation 113 caused by kidneys in a failing condition. This decrease in stimulation by the kidneys is expected to decrease the vasoconstriction 114 in the patient's circulatory system, and decrease the amount of sodium and fluid retention 115 in the patient. In turn, increased urine output, reduced vasoconstriction, and decreased sodium level should restore normal fluid balances in the patient, improve oxygenation of the blood and decrease the heart workload 116. Heart function should improve 117 due to the reduction in its workload and the other beneficial effects due to renal perfusion. Moreover, a stronger heart and higher blood pressure will improve the perfusion of other organs 118 and thereby normalize the acid-base metabolism 119 to further improve the workload, etc. on the heart.

The system for treating CHF disclosed here restores kidney functioning and thereby breaks the cycle between heart and kidney failure. This type of CHF treatment is new, novel and unobvious. Moreover, this treatment may be used in connection with other CHF treatments that directly treat the heart, and may be used for both chronic and acute CHF.

For treating acute CHF, an invasive catheter system has been developed by applicants to perfuse the kidneys. This catheter system is described more fully in the co-owned and related U.S. application Ser. No. 09/454,605 for a "Kidney Perfusion Catheter", identified above. The catheter is inserted at the patient's groin and into the femoral artery. The catheter maneuvered by a surgeon through the femoral artery, into the aorta to the entrance of one of the renal arteries. Blood enters a proximal end of the catheter from a blood pump and flows from the distal end of the catheter directly into the renal artery. This blood flow perfuses the kidney and rapidly restores adequate kidney functions to one kidney.

Apparatuses for treating chronic CHF may include an implantable device, e.g., using a prosthesis vein or artery, having a distal end coupled to one of the renal arteries and a proximal end coupled to a fluid port implanted under the patient's skin. Kidneys reside deep in the body and cannot be reached easily from the body surface with a needle or a catheter. To perfuse the kidney, a conduit to a blood pump is attached to the patient's fluid port coupling to cause blood to flow from the pump through the implanted device to the renal artery. The patient is connected to the blood pump periodically to perfuse the kidney, without having to surgically insert a catheter into the patient.

Alternatively, a blood pump and passageway between a vein and a renal artery may be implanted in a patient. The blood pump controls a flow of blood from the vein, through the passageway, and into the renal artery to perfuse the kidney. The blood pump may be remotely controlled by the patient or doctor to operate periodically to perfuse the kidney. More detailed descriptions of implantable devices are disclosed in the commonly-owned PCT Application No. WO 01/97879 entitled "Apparatus And Method for Perfusing The Kidney With Venous Blood"; PCT Application No. WO 01/97717 entitled "Implantable Flow Diversion Device"; PCT Application No. WO 01/97878 entitled "Split Circulation Device"; PCT Application No. WO 01/97717 entitled "Instrumented Stent"; U.S. Pat. No. 6,241,743 entitled "Anastomosis Device And Method".

SUMMARY OF THE DRAWINGS

A preferred embodiment and best mode of the invention is illustrated in the attached drawings that are described as follows.

DETAILED DESCRIPTION OF A PREFERRED EMBODIMENT OF THE INVENTION

Figure 1:
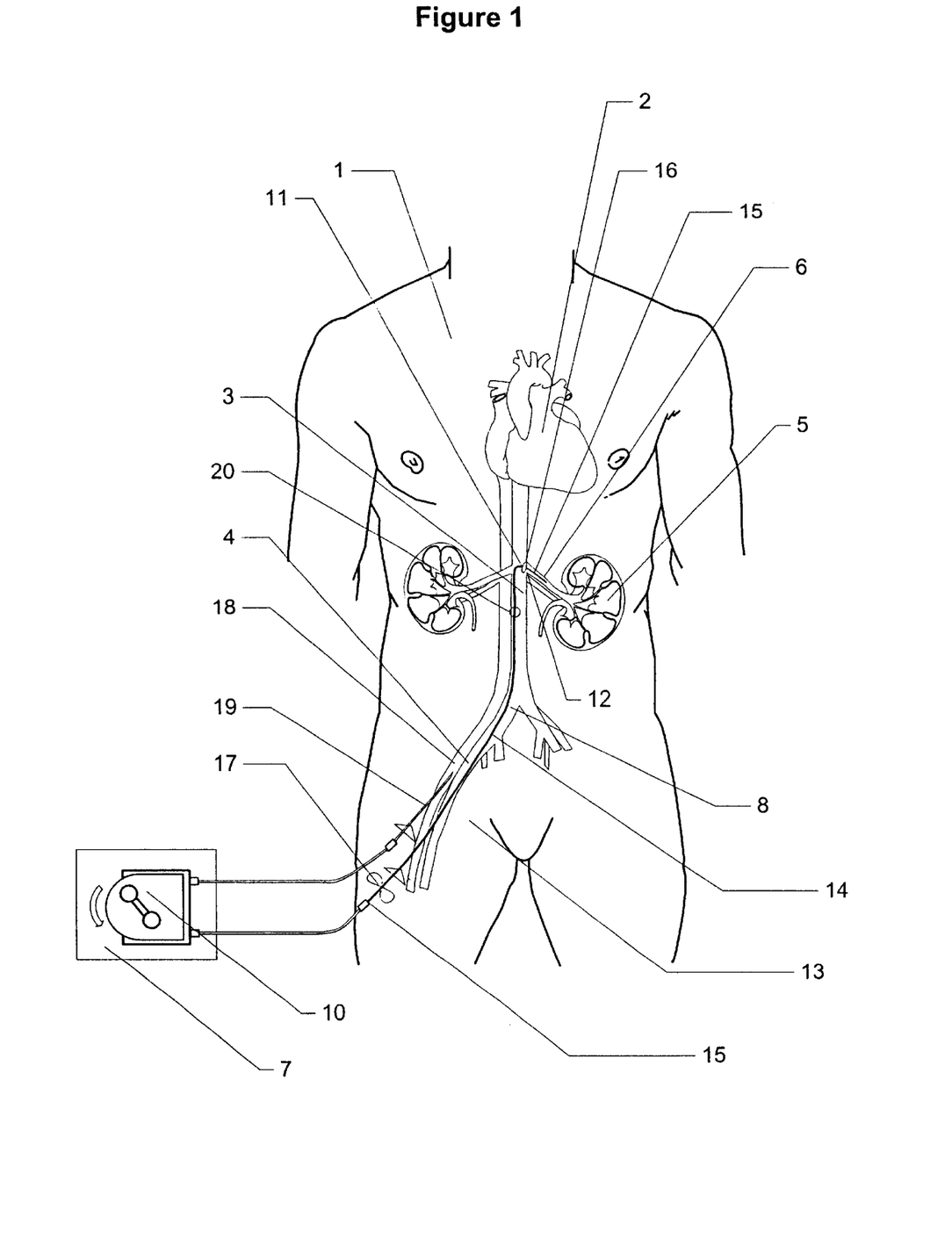
FIG. 1 is a graphical illustration of a patient being treated for CHF by perfusing a kidney with a perfusion catheter and blood pump.

FIG. 1 is a schematic diagram of a patient 1 having a heart 2, an aorta 3, a femoral artery 4, a kidney 5 and a renal artery 6. The patient is suffering from congestive heart failure (CHF) and his heart is unable to maintain sufficient blood pressure in his circulatory system to maintain normal kidney functions. Due to the failing heart, blood flowing from the aorta into the renal artery lacks sufficient pressure to be filtered through the kidney. If the CHF is acute and the patient requires immediate treatment, then a clinical in-situ kidney perfusion catheter apparatus, such as is shown in FIG. 1, may be used to increase the blood pressure in the renal artery and perfuse the kidney with blood.

The kidney perfusion apparatus 7 pumps blood directly into the renal artery at sufficient pressure and volume to perfuse at least one of the kidneys and restore at least a nominal amount of the patient's kidney function. This method of artificially perfusing the kidney with a perfusion catheter apparatus treats acute CHF by (i) restoring nominal kidney function, (ii) reducing fluid build-up in the body, (iii) cleansing the blood of salt, urine and other toxins, (iv) reducing the output by the kidney of neurohormonal distress signals causing vasoconstriction in the patient's circulatory system, e.g., blood vessels, and (v) reducing pumping demands on the heart by providing supplemental blood pressure via the blood pump.

Blood is withdrawn from the patient using a withdrawal catheter inserted into a vein or artery of the patient, such as in the femoral artery or vein. The blood is conducted to the pump using common tubing compatible with long term exposure to blood such as Tygon or silicon tubing.

The pump may be a roller or a centrifugal mechanism such as the ones used to pump blood for dialysis or in a heart lung machine. The pump may also be extracorporeal or implanted as the kind of pump previously disclosed in PCT Application No. WO 01/97879 entitled "Apparatus and Method for Perfusing the Kidney with Venous Blood". Further, the pump can be of any type (such as an axial or rotary flow pump) that is capable of raising the pressure of the blood to the desired value.

The pump elevates the blood pressure and ejects blood into another catheter. This infusion catheter will be placed in the patient's renal artery using common fluoroscopic technique or using a permanently implanted graft, such as that disclosed in the above-identified PCT Application No. WO 01/97717 entitled "Implantable Flow Diversion Device";

PCT Application No. WO 01/97878 entitled "Split Circulation Device"; PCT Application No. WO 01/97687 entitled "Instrumented Stent"; and U.S. Pat. No. 6,241,743 entitled "Anastomosis Device And Method".

An exemplary renal artery perfusion catheter 8 has a proximal end 9 attached to a blood pump 10 and a distal end 11 positioned in a renal artery 6 at the inlet (ostium 12) of one of the kidneys 5. As the catheter 8 is moved by a surgeon from the insertion point at the groin 13 and through the femoral artery 4, into the aorta 3, it makes a sharp turn at the renal artery branch 6, passes through the ostium and into the renal artery 6.

The catheter 8 may include an introducer catheter 14, have a terminating end at the inlet to the ostium 12, and have a smaller diameter and short catheter tip 15 telescoping from the introducer catheter and into the renal artery. The introducer catheter may have a sealing balloon 16 blocking the inlet to the ostium and the catheter tip may have a partitioning balloon that partially occludes the renal artery during perfusion, so as to prevent reverse blood flow from the catheter tip out the renal artery and into the aorta. A more detailed description of a perfusion catheter assembly is disclosed in the previously identified PCT Application No. WO 01/41861 entitled "Kidney Perfusion Catheter".

Blood, at a higher pressure than provided by the patient's heart, is supplied to the perfusion catheter by the blood pump 10 which is connected to the proximal end 9 of the catheter with a locking connector 17. The supply of blood to the pump drawn from a femoral vein 18 of the patient 1. Blood is withdrawn using a cannula catheter 19 inserted into the femoral vein or, alternatively is drawn from the femoral artery using an attachment to the perfusion catheter. The pump 10 increases the kinetic energy of the blood, e.g., increases the pressure and/or velocity of the blood, and passes the blood to the perfusion catheter 7 which ejects the blood into the renal artery from tip 11 of the catheter.

The blood ejected from the catheter tip increases the pressure of the blood flowing through the renal artery to the kidney. Using the perfusion apparatus 7, the blood flow entering the kidney 5 has sufficient flow and pressure to cause the kidney to resume normal functioning (or at least adequate functioning), including removing excess body fluids, sodium and other toxins, and increasing urine flow. In addition, a partitioning element, e.g., sealing balloon 16, on the shaft of the distal end 11 of the introducer catheter 14 prevents injected blood from running off into the aorta where pressure is lower. Also, the introducer catheter 14 may have a positioning device(s) to anchor the distal end of the perfusion catheter at the entrance of the renal artery. These positioning devices may include a semi-rigid portion at the distal region of the introducer catheter that recoils to a hook shape that bows across the diameter of the aorta 3 and a positioning bulb 20 that provides a bumper between the introducer catheter 14 and the vessel wall of the aorta 3.

Figure 2:
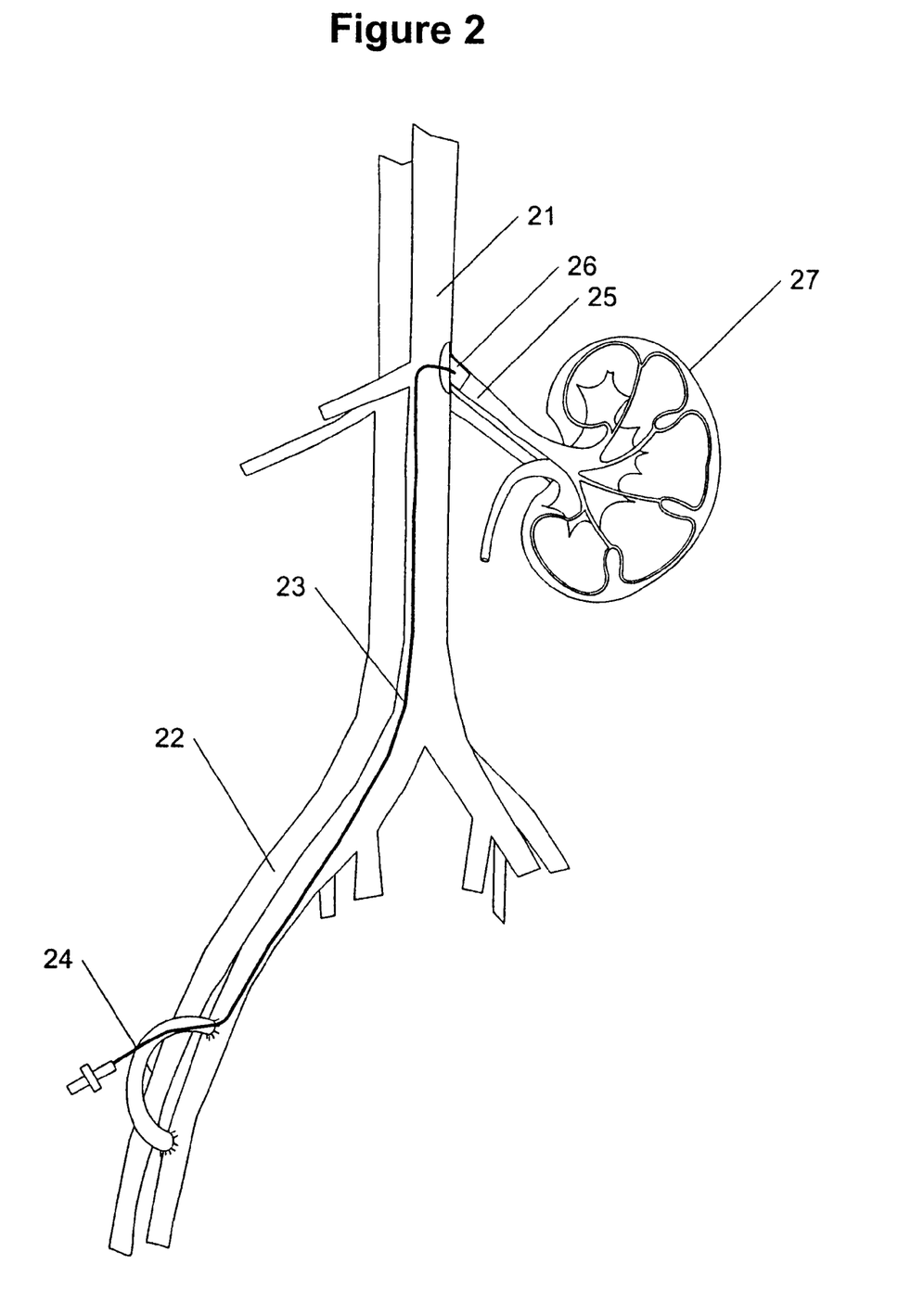
FIG. 2 is a diagram illustrating a perfusion system for administering periodic CHF treatment using a renal stent.

For patients with chronic CHF who require regular perfusion treatment of their kidney(s), a graft may be surgically implanted in permanent connection to the femoral artery of a patient to provide an easily and repeatedly accessible conduit to insert the perfusion catheter, as is shown in FIG. 2 The apparatus shown in FIG. 2 is an embodiment of periodic treatment of CHF by augmented renal perfusion. The patient has an aorta 21 and a kidney 27 connected with the renal artery 25. A special vessel prosthesis or stent 26 is implanted using minimally invasive surgical or intravascular technique in the ostium of the renal artery. Another prosthesis or graft 24 is implanted to form a conduit in connection to the femoral artery 22. A catheter 23 can be introduced via the graft 24 into the renal artery ostia stent 26. The graft also provides a seal to reduce bleeding into the femoral artery 22 and aorta 21. Since the stent 26 protects the sensitive renal artery from trauma, catheterization does not require an interventionalist and a costly catheterization laboratory. The cardiologist navigates the catheter using simple imaging means means, such as ultrasound, MRI or may even perform the procedure blindly using a special guidance system. The one time minor operation of implanting a stent and graft decreases the risk and cost of repetitive treatments, and eliminates the necessity of repeated surgical procedures. The catheter 23 and stent 26 may include a guidance system such as magnetic, infrared or ultrasonic means to navigate the procedure and indicate the relative position of the catheter tip and the stent. A graft 24 in the groin of the patient reduces damage to the femoral artery done by repetitive punctures and makes procedures more comfortable for the patient. The graft may be formed as a loop returning blood to the artery so that there will always be flow in the graft and it will not clot.

Figure 3:
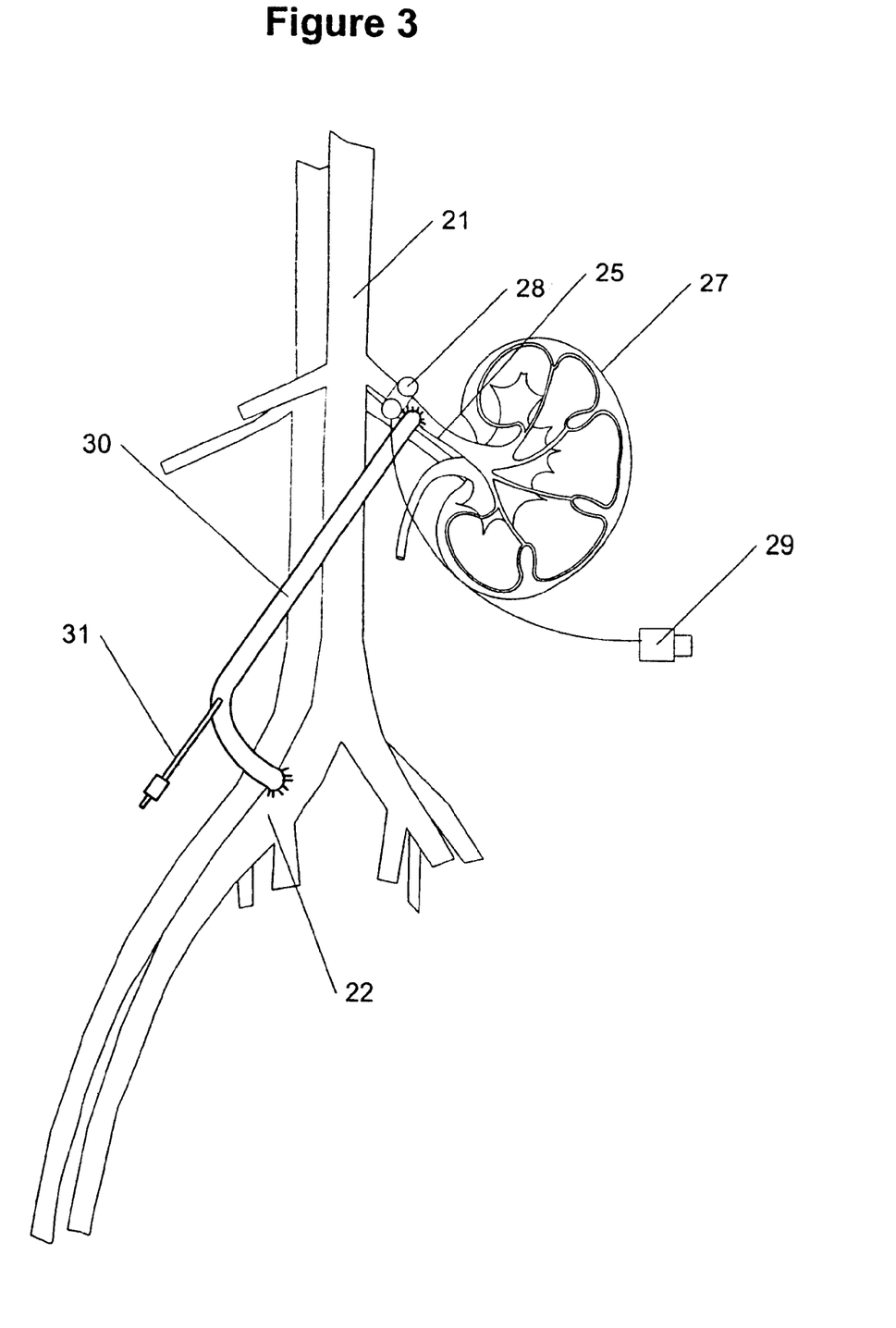
FIG. 3 is a diagram illustrating a perfusion system for administering periodic CHF treatment using tunnel graft and renal artery occluder.

Another embodiment of the periodic treatment apparatus is shown in FIG. 3. A permanent graft or tunnel 30 connects the renal artery 25 to the femoral artery 22 or other convenient blood vessel. Part of the tunnel graft is routed close to the skin where a nurse can easily insert catheter or needle 31 into the graft for repeated kidney perfusion treatments. A Catheter or needle 31 is connected to the perfusion pumping apparatus, such as shown in FIG. 1. To prevent blood flow directed towards perfusing the kidney from running off from the renal artery and into aorta 21, an occluder 28 is placed surgically around the renal artery 25 proximal to the graft attachment. During each perfusion treatment, the occluder may be inflated by pump 29 that can be extracorporeal or implanted under the skin. When inflated, the doughnut shaped occluder closes the renal artery for the duration of treatment. At the conclusion of the treatment, the occluder is deflated and the catheter removed from the tunnel graft.

A graft technique may be useful for patients that are in the advanced stage of CHF heart failure and are frequently admitted to the hospital with an acute worsening of their condition. A graft technique is partially disclosed in more detail in PCT Application No. WO 01/97717 entitled "Implantable Flow Diversion Device". When equipped with the graft, these patients may not require admission to the intensive care unit (ICU) of a hospital and could be treated on an outpatient basis.

To prevent clotting of blood in and around the permanent graft, the graft could be implanted as a shunt between the renal artery and a vein. Small amounts of blood will be allowed to flow through the graft all the time to prevent clotting. At the time of the treatment, a catheter or a needle will be inserted into the graft. This will reduce the cost and risk of treatment dramatically in comparison to the catheter method utilized in acute CHF as described above. An exemplary shunt is disclosed in the above-identified PCT Application No. WO 01/97717 entitled "Instrumented Stent".

Ultimately, for patients that need continuous CHF treatment to keep their kidneys alive and potentially to reverse the heart failure state, an implantable or partially implantable pump can be surgically positioned in the patient in a manner similar to the implanting of the well known left ventricular support device or LVAD. Examples of LVADs suitable for renal perfusion are disclosed in PCT Application No. WO 01/97878 entitled "Split Circulation Device", and U.S. Pat. No. 6,241,743 entitled "Anastomosis Device And Method".

After the perfusion device 7 is connected, a physician starts the pump. Blood is introduced into the patient's renal artery under pressure controlled by the operator. This pressure will determine the desired GFR and urine output. The physician may desire to adjust the perfusion pressure based on clinical information to optimize the treatment. Alternatively, clinical data could be input directly into the apparatus equipped with a computer program to optimize the treatment. Clinical data could include, but is not limited to, the systemic blood pressure, cardiac output, central venous blood pressure (CVP), blood oxygen saturation, urine output, GFR, other hematological or biochemical parameters, and patient's weight.

The objective of the acute treatment is to remove fluid from the patient as fast as is safe while also protecting the patient's kidney. It is commonly known from the use of diuretics and hemofiltration in acute heart failure patients that there is danger in removing fluid too rapidly. The significant amount of extra fluid that burdens heart failure patients is stored in the space outside of the blood vessels (e.g., in the tissue) and cannot be mobilized quickly.

Heart failure patients require a certain amount of preload or heart filling pressure for their weakened heart to pump adequate amounts of blood. These factors dictate that the unwanted fluid shall be removed from these patients slowly with care as to not make them hypotensive. Information about hypotension can be derived from mean arterial pressure based on absolute values of the patient's previous history. In addition, a physician may use the perfusion device 7 to maintain the optimal preload (heart filling venous pressure) for cardiac function in a CHF patient.

A physician inputs the desired arterial blood pressure and or venous pressure and the perfusion device adjusts the renal perfusion pressure slowly to remove fluid at the rate that will result in the desired pressure. The venous pressure set too high could result in peripheral edema and organ dysfunction. Venous pressure set too low can result in the undesired reduction of cardiac output and blood pressure. On a more simple level, the physician could command the machine to remove a set amount of fluid from the patient over a set number of hours at the maximum safe rate. The physician can adjust that target based on the patient's blood pressure or weight measurements. Since the response of each patient's kidney to pressure will be different, the patient's weight will need to be monitored, or more conveniently, the device will be equipped with ways to measure the weight or volume of excreted urine. For example, sensors can be incorporated in stents to monitor and other important variables as disclosed in PCT Application No. WO 01/97687 entitled "Instrumented Stent". If venous blood is used to perfuse the kidney the withdrawal catheter could be instrumented with a pressure sensor.

The method for treating CHF described here may be used to stabilize, improve or restore normal or adequate kidney function in the setting of low blood pressure and flow, in particular allowing enhanced patient fluid removal, modulation of the renin-angiotensin system and other neurohormonal substances, treatment of, improvement in or prevention of the occurrence of chronic and/or acute CHF. It can, however, refer to any temporary or permanently fully or partially implantable perfusion system used in the treatment of heart failure.

The treatment method may also allow the proper monitoring and detection of alterations in kidney and circulatory function. The described method also allows physicians to add therapeutic agents directly to the blood stream of the kidney by providing a catheter or implanted devices that pumps blood to the renal artery. This ability to introduce therapeutic agents to the blood flow allows physicians to maintain, improve, or help restore kidney or overall circulatory function. Such agents may include diuretics and vasodilators or be one or more other therapeutic agents, selected from the group consisting of angiotensin converting enzyme (ACE) inhibitors, beta-blockers, cardiac glycosides and/or other commonly known pharmacological or mechanical therapeutic modalities. Significantly, they can be introduced into the blood system in much smaller dosages than would be required if the medicine was given systemically. In this way, the beneficial effects of the treatment can be achieved minimizing any deleterious side effects or toxicity.

Figure 4:
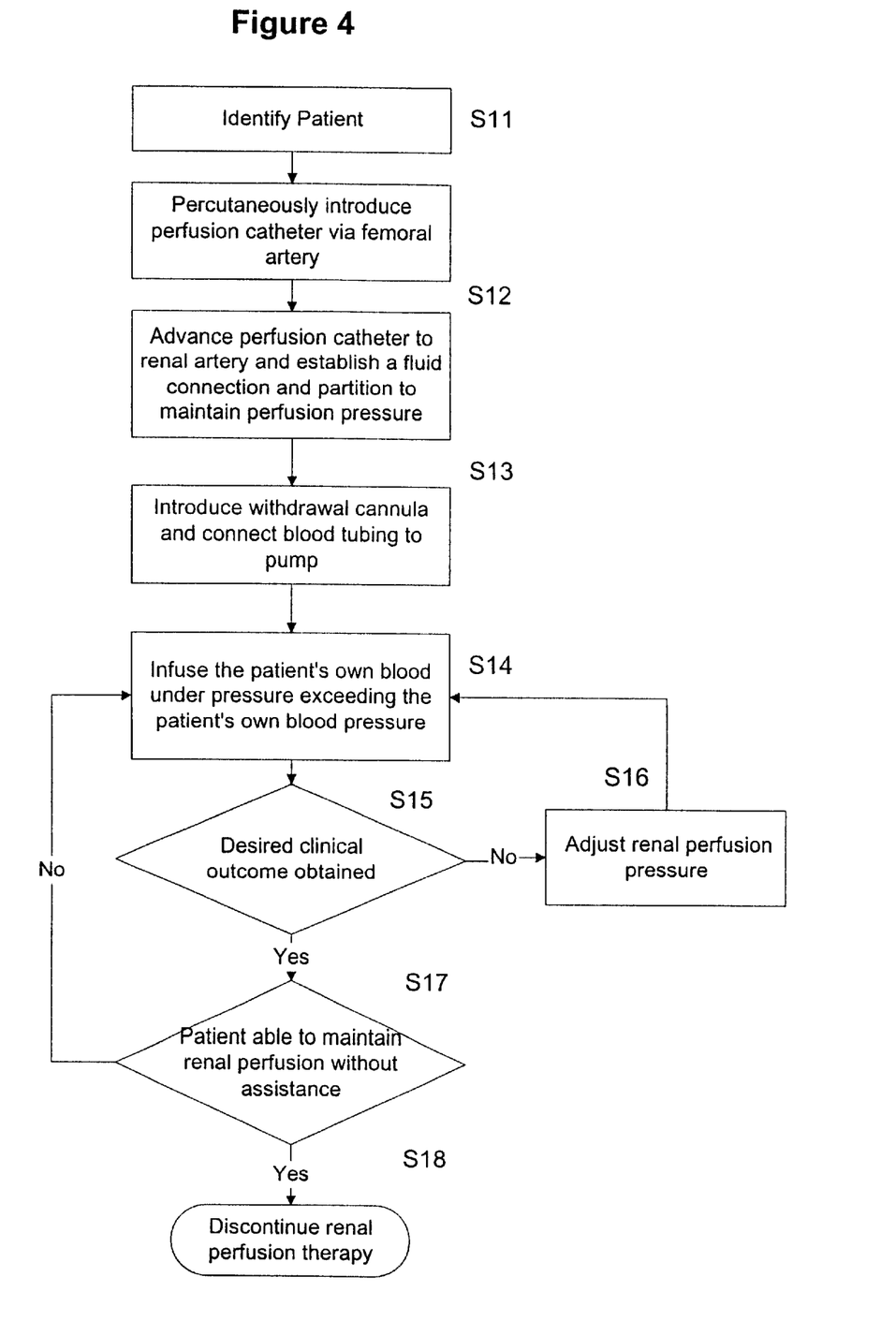
FIG. 4 is a flow chart for a method of perfusing a patient's kidney to achieve a desired condition of the patient.

FIG. 4 is a flow chart for a method of perfusing a patient's kidney to achieve a desired condition of the patient. The patient with CHF is identified, in step S11, and prepared for percutaneous introduction of the perfusion catheter 8 or needle 31 via a femoral artery 4 or graft tunnel 30 at step S12. Once inserted, the distal end 11 of the perfusion catheter is advanced to a renal artery 6 to establish fluid connection and maintain perfusion pressure to the kidney 5. At this step seals and occlusion devices are activated to form the alternative fluid path. At S13, a cannula or withdrawal catheter 19 is introduced into the femoral vein 18 to provide fluid connection to allow infusion of the patient's own blood under a pressure via the kidney perfusion apparatus 7 and blood pump 10. Although the femoral vein is used by way of illustration in the preferred embodiment the blood donor vessel utilized may be either a vein or an artery. Once the fluid communication is established, perfusion pressure will be adjusted to restore the filtration functions of the kidney and augment blood pressure up to the autoregulatory range of the patient's kidney, at S14. At S15, the patient will be monitored to determine if the desired clinical outcomes of removing the desired amount of fluid over the desired time, improving glomerular filtration rate, increasing urine output, blood pressure and decreasing the compensatory response mechanisms of the rennin angiotensin system are obtained. If the desired clinical outcomes are not achieved renal perfusion pressure will be adjusted at a step S16. At S17, if the patient is able to maintain renal perfusion without the assistance of the renal perfusion pump and apparatus, then renal perfusion therapy is discontinued, at a step S18.

Figure 5:
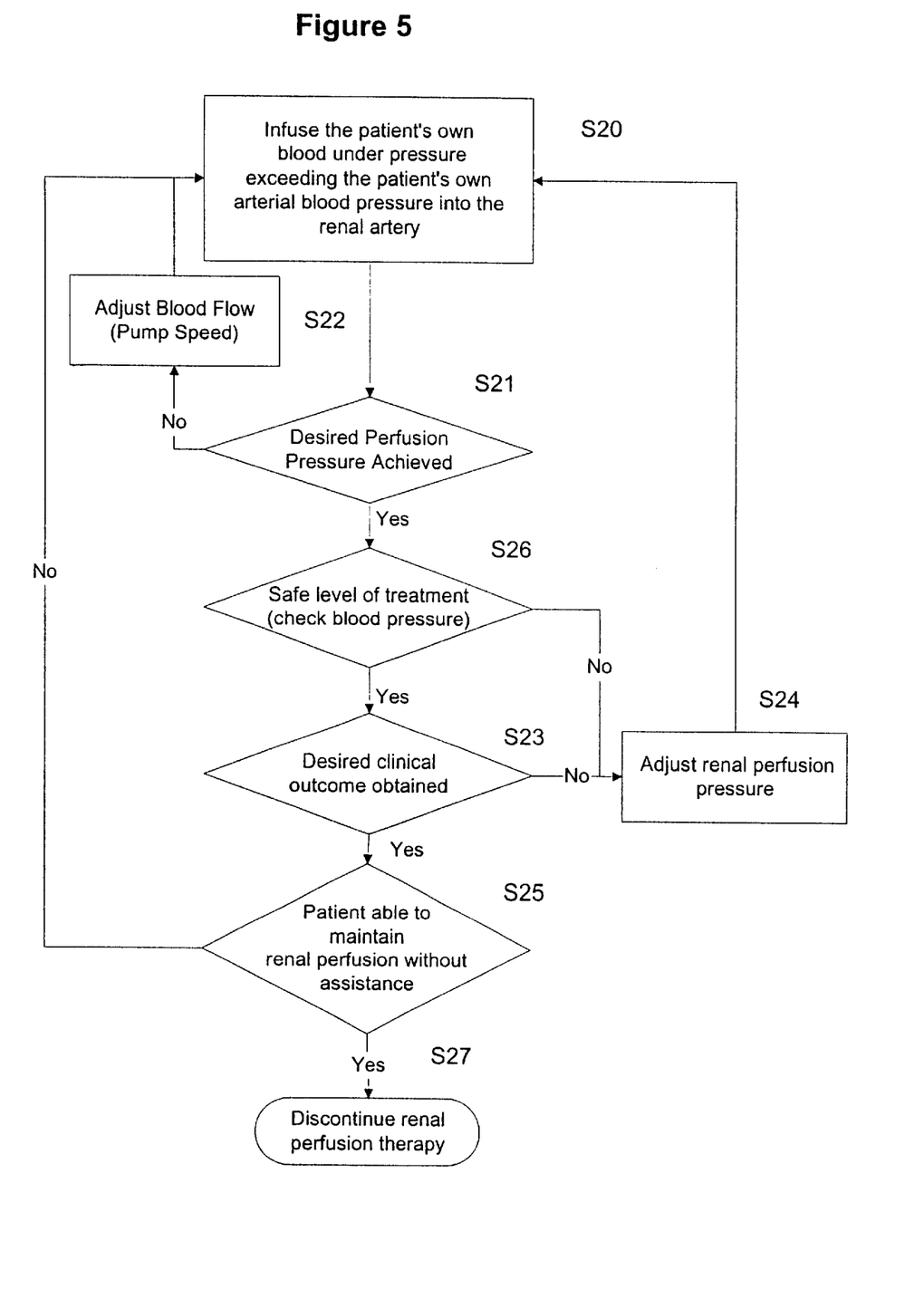
FIG. 5 is a flow chart for another embodiment of a method of perfusing a patient's kidney to achieve a desired condition of the patient.

FIG. 5 is a flow chart of a second embodiment of a CHF treatment method in which both a desired renal pressure and a desired clinical outcome are predetermined. Also safe limit of treatment (rate of fluid removal) is tested. In step S20, which corresponds to steps S11 to S14, a kidney of a patient is infused with a perfusion fluid, e.g., blood, at an elevated pressure. The method first determines whether the predetermined perfusion pressure has been achieved in S21. Pressure sensors at the proximal end 9 of a perfusion catheter may measure a flow pressure which can be converted to an estimated renal perfusion pressure, using standard fluid dynamic algorithms that take into account the viscous effects of the perfusion catheter on the flow of blood to the renal artery. If the calculated perfusion pressure does not fall within an acceptable range of the predetermined pressure, for example 100 mm Hg+/−10 mmHg, then the blood pump speed is adjusted to achieve the desired perfusion pressure, in S22. It is believed that until the desired renal pressure is achieved, that normal kidney functions will not result. Accordingly, steps S21 and S22 ensure that the proper fluid pressure is applied to perfuse the kidney such that the kidney will resume its normal filtering function.

A safe level of fluid removal is maintained by comparing a clinical parameter, for example central venous pressure (CVP) or systemic artereial pressure or both to minimum allowed at step S26. If CVP is approaching an unsafely low level, for example 10 mmHg, renal perfusion pressure can be adjusted on step S24. This way fluid will be removed at the maximum rate without causing hypotension.

Once an appropriate safe level of perfusion pressure is achieved, then the patient is monitored for urine output, fluid status, edema, pulmonary wedge pressure or other desired clinical outcome in S23. A computer that is a part of the device can perform such monitoring. Alternatively the device operator can make measurements and enter them into the system via keyboard. For example, blood pressure can be monitored every second using common blood pressure monitor, while urine output (by weighting the urine collection bag) can be measured every ten minutes. Patient's weight can be monitored every four hours to correct other measurements.

If the desired clinical outcome is not achieved within a predetermined period of time, e.g., four to eight hours, then desired (or predetermined) perfusion pressure to the kidney is readjusted in hopes of restoring kidney function, in S24. For example, the desired pressure may be incrementally increased by 10 or 20 mmHg. Each time the perfusion pressure is adjusted, the method first checks that the measured renal perfusion pressure matches the current setting of the desired perfusion pressure. Once the perfusion pressure is properly set, then the method monitors the patient for safe limit then for a desired clinical outcome.

Renal blood flow is regulated by neurohormonal feedbacks of the body within a broad range of 200 to 600 mL/min. Vascular resistance of the kidney can be expected to change continuously. The servomechanism of the pump will maintain perfusion pressure on target by manipulating the pump speed while allowing the kidney to adjust to the changing neurohormonal milieu.

Once the desired clinical outcome is reached, e.g., sufficient volume of fluid has been removed, then the patient is checked for whether he can maintain renal perfusion without assistance, in S25. To determine whether the patient can naturally maintain urine output, a doctor may temporarily discontinue or markedly reduce the blood pump after determining that the kidneys have achieved the desired clinical effect, e.g., urine flow, blood pressure, or fluid volume with artificial perfusion. If the patient maintains the desired clinical outcome for some minimum period, e.g., four to eight hours during which an adequate amount of urine flow continues, then the doctor can discontinue perfusion treatment to the patient. If the patient does not maintain the desired clinical outcome after artificial perfusion is stopped, the artificial perfusion of the kidney can continue.

Once the kidney begins normal functioning and reduces the load on the heart by eliminating excess body fluid and blood toxins, the heart may be unloaded sufficiently to naturally increase the blood pressure to the kidneys at a level sufficient to sustain kidney functioning. In that case, the treatment has succeeded and the patient is removed (at least temporarily) from artificial perfusion devices and treatment. In other cases a patient may require another treatment in several weeks or months.

The invention has been described in connection with what is presently considered to be the most practical and preferred embodiment. The invention is not limited to the disclosed embodiment. The invention covers various modifications and equivalent arrangements included within the spirit and scope of the appended claims.

What is claimed is:

1. A method to treat congestive heart failure in a patient comprising the steps of:

a. artificially perfusing at least one kidney in the patient with a perfusion fluid by withdrawing venous blood from the patient and infusing as the perfusion fluid the blood withdrawn from the patient into at least one kidney;

b. restoration of a predetermined functional level of renal function of said kidney;

c. ceasing the artificial perfusing step after the predetermined functional level has been achieved, or a predetermined time of treatment has elapsed.

2. A method to treat congestive heart failure as in claim 1 wherein steps (a), (b) and (c) are repeated on a periodic basis to treat chronic congestive heart failure.

3. A method to treat congestive heart failure as in claim 2 the periodic basis is an intermittent repetition of steps (a), (b) and (c) over a period of up to six weeks.

4. A method to treat congestive heart failure as in claim 1 wherein steps (a), (b) and (c) are performed to treat acute congestive heart failure.

5. A method to treat congestive heart failure as in claim 1 wherein step (a) is performed for a short-term period of less than 24 hours before step (b) is achieved.

6. A method to treat congestive heart failure as in claim 1 wherein step (a) is performed for a short-term period of less than three days before step (b) is achieved.

7. A method to treat congestive heart failure as in claim 1 wherein the restoration of a baseline renal function comprises returning a normal perfusion pressure to the at least one kidney after step (a).

8. A method to treat congestive heart failure as in claim 1 wherein said kidney is perfused in step (a) and a second kidney of the patient is not perfused.

9. A method to treat congestive heart failure as in claim 1 wherein both kidneys are in the patient having two kidneys.

10. A method to treat congestive heart failure as in claim 1 wherein step (a) is performed by an implanted blood pump in the patient that provides the perfusion fluid to the at least one kidney.

11. A method to treat congestive heart failure as in claim 1 wherein the perfusion blood is a mixture of venous and arterial blood.

12. A method to treat congestive heart failure as in claim 1 further comprising the step of controlling a pressure of the perfusion fluid in step (a) such that the pressure is within a normal autoregulatory range of a perfusion pressure for the at least one kidney.

13. A method to treat congestive heart failure as in claim 1 further comprising the step of controlling a pressure of the perfusion fluid in step (a) such that the pressure is higher than the normal autoregulatory range but lower than the pressure that will cause barotrauma of the kidney.

14. A method to treat congestive heart failure as in claim 1 wherein the baseline renal function is determined by monitoring a urine output of the patient.

15. A method to treat congestive heart failure as in claim 1 wherein the functional level is a baseline renal function that is determined by monitoring a blood pressure of the patient.

16. A method to treat congestive heart failure as in claim 15 wherein the blood pressure being monitored is arterial pressure.

17. A method to treat congestive heart failure as in claim 15 wherein the blood pressure monitored is venous blood pressure.

18. A method to treat congestive heart failure as in claim 1 wherein the predetermined functional level is a baseline renal function that is determined by monitoring the weight of the patient.

19. A method to treat congestive heart failure in a patient comprising the steps of:
 a) artificially perfusing at least one kidney in the patient with a perfusion fluid having a perfusion fluid pressure;
 b) adjusting the perfusion fluid pressure to fall within a predetermined pressure range;
 c) monitoring the patient for a predetermined desired improvement in a condition related to the congestive heart failure;
 d) if the desired improvement is not achieved, then changing the predetermined pressure range and repeating steps (a) and (b) until the improvement is achieved.

* * * * *